United States Patent
Mok et al.

(10) Patent No.: US 8,966,698 B2
(45) Date of Patent: Mar. 3, 2015

(54) BRUSH HEAD FOR AN ELECTRIC TOOTHBRUSH

(71) Applicant: Techtronic Floor Care Technology Limited, Tortola (VG)

(72) Inventors: Kwok Ting Mok, Kowloon (CN); Wai Tong Chan, Tsing Yi (CN)

(73) Assignee: Techtronic Floor Care Technology Limited, Tortola (VG)

( * ) Notice: Subject to any disclaimer, the term of this patent is extended or adjusted under 35 U.S.C. 154(b) by 0 days.

(21) Appl. No.: 13/921,244

(22) Filed: Jun. 19, 2013

(65) Prior Publication Data
US 2014/0143962 A1 May 29, 2014

(30) Foreign Application Priority Data
Nov. 27, 2012 (HK) .................................. 12112151

(51) Int. Cl.
 *A61C 17/26* (2006.01)
 *A61C 17/34* (2006.01)
(52) U.S. Cl.
 CPC ............... *A61C 17/26* (2013.01); *A61C 17/34* (2013.01); *A61C 17/3436* (2013.01); *A61C 17/349* (2013.01)
 USPC .............................................. 15/22.1; 15/28
(58) Field of Classification Search
 USPC ........................................ 15/22.1, 28, 167.1
 See application file for complete search history.

(56) References Cited

U.S. PATENT DOCUMENTS

| 2,142,933 | A | * | 1/1939 | Bickford ........................ 15/50.1 |
| 2,668,968 | A | | 2/1954 | Dobrowolski |
| 4,845,795 | A | | 7/1989 | Crawford et al. |
| 5,382,221 | A | * | 1/1995 | Hsu et al. ...................... 601/114 |
| 7,266,855 | B2 | | 9/2007 | Zhuan |
| 8,316,496 | B2 | * | 11/2012 | Al-Qaffas ........................ 15/22.1 |
| 8,516,642 | B1 | * | 8/2013 | Farahat ........................... 15/22.1 |
| 2010/0330538 | A1 | * | 12/2010 | Salazar et al. ................. 433/216 |

FOREIGN PATENT DOCUMENTS

JP  59081054 A  *  5/1984

* cited by examiner

*Primary Examiner* — Shay Karls
(74) *Attorney, Agent, or Firm* — Michael Best & Friedrich LLP

(57) ABSTRACT

A brush head for an electric toothbrush includes a housing and a plurality of bristle tufts extending through apertures in the housing. A gear train within the housing includes a drive gear configured to oscillate about an axis, and a plurality of first driven gears. Each first driven gear is meshed directly with the drive gear. Drive means are configured to provide motion to the gear train. The drive gear provides a first drive output including a first oscillating motion in a first direction. The driven gears each provide a second drive output including a second oscillating motion in a second direction which is opposite to the first direction.

12 Claims, 6 Drawing Sheets

US 8,966,698 B2

BRUSH HEAD FOR AN ELECTRIC TOOTHBRUSH

CROSS-REFERENCE TO RELATED APPLICATIONS

This application claims priority to Hong Kong Short Term Patent Application No. 12112151.6, filed Nov. 27, 2012, the entire contents of which are incorporated by reference herein.

FIELD OF INVENTION

The present invention relates to a toothbrush, in particular, an electric toothbrush.

BACKGROUND OF THE INVENTION

Electric toothbrushes are well known. Similar to manual toothbrushes, an electric toothbrush typically includes a handle attached to a brush head. The brush head usually consists of one or more tufts of bristles which are used to clean the teeth and gums. Electric toothbrushes use electric power supplied usually by a battery to move the brush head rapidly, rotating and/or oscillating the bristle tufts to clean plaque and tarter build up on the teeth and gums. Due to the geometry and alignment of teeth, there are often areas in the mouth that are difficult to access and therefore difficult to clean.

Typically, the usual cleaning technique is to simply move the electric toothbrush slowly from tooth to tooth, allowing the rotating/oscillating brushes to do most of the work. Since, tooth orientation varies from user to user, it is desirable to improve the effectiveness of the electric toothbrush to maximize cleaning.

SUMMARY OF THE INVENTION

One embodiment of the present invention provides a brush head for an electric toothbrush. The brush head includes a housing and a plurality of bristle tufts extending through one or more apertures in the housing. The brush head includes a gear train within the housing. The gear train includes a drive gear configured to oscillate about an axis, and a plurality of first driven gears wherein each first driven gear is meshed directly with the drive gear. The brush head includes drive means configured to provide motion to the gear train. The drive gear provides a first drive output including a first oscillating motion in a first direction, and the driven gears each provide a second drive output including a second oscillating motion in a second direction which is opposite to the first direction.

Preferably, the plurality of first driven gears includes two first driven gears disposed around a first quadrant of the drive gear.

Preferably, the plurality of first driven gears further includes two first driven gears disposed around a second quadrant opposite the first quadrant of the drive gear.

Preferably, the gear ratio between the drive gear and each first driven gear is 4.

Preferably, the gear train includes a plurality of second driven gears meshed with one or more first driven gears.

Preferably, the plurality of bristle tufts includes a first set of bristle tufts attached to the drive gear and a second set of bristle tufts attached to each driven gear.

Preferably, the first set of bristle tufts are shorter than the second set of bristle tufts and wherein the first set of bristle tufts includes bristle tufts having a flat tip and each second set of bristle tuft includes bristle tufts having a tapered tip.

Another embodiment of the present invention provides a brush for an electric toothbrush wherein the brush head includes a housing and a plurality of bristle tufts extending through one or more apertures in the housing. The brush head includes an epicyclic gear set within the housing. The gear set includes a ring gear and plurality of planet gears supported on a planet carrier. Each planet gear is meshed with the ring gear. The brush head includes drive means configured to provide motion to the epicyclic gear set. A first drive output includes a first oscillating motion about a first axis, and a second drive output including an orbiting motion about the first axis and a second oscillating motion.

Preferably, the drive means includes a drive shaft having a first end connected to a motor and a second end connected to the planet carrier so that in use the planet carrier is driven by the drive shaft.

Preferably, the plurality of bristle tufts includes a first set of bristle tufts attached to the planet carrier and a second set of bristle tufts attached to each planet gear.

Preferably, the brush head further includes a sun gear, and each planet gear is meshed between the sun gear and the ring gear.

Preferably, the ring gear is fixed and the sun gear and the planet carrier oscillate about the first axis causing the planet gears to orbit about the first axis and oscillate about their own respective axes.

Preferably, the gear ratio between the ring gear and the planet gear is 5, and the gear ratio between the sun gear and the planet gears is 3.

Preferably, the plurality of bristle tufts includes a first set of bristle tufts attached to the sun gear and a second set of bristle tufts attached to each planet gear.

BRIEF DESCRIPTION OF THE DRAWINGS

Preferred forms of the invention will now be described by way of example with reference to the accompany drawings.

DETAILS DESCRIPTION OF A PREFERRED EMBODIMENT

Figure 1:
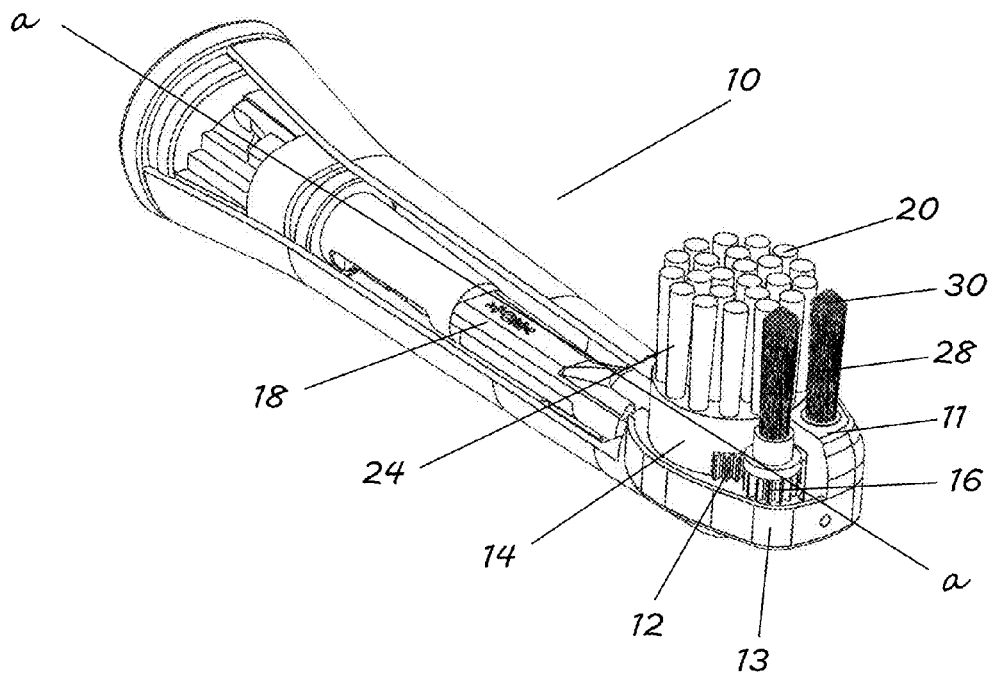
FIG. 1 is a perspective view of a brush head according to one embodiment of the present invention.
Figure 3:
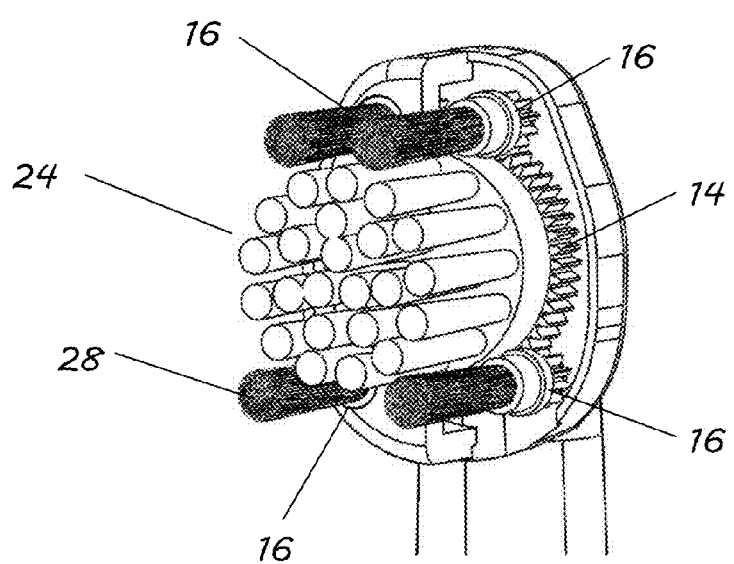
FIG. 3 is a partial view of a brush head according to another embodiment of the present invention.
Figures 4, 5, 6:
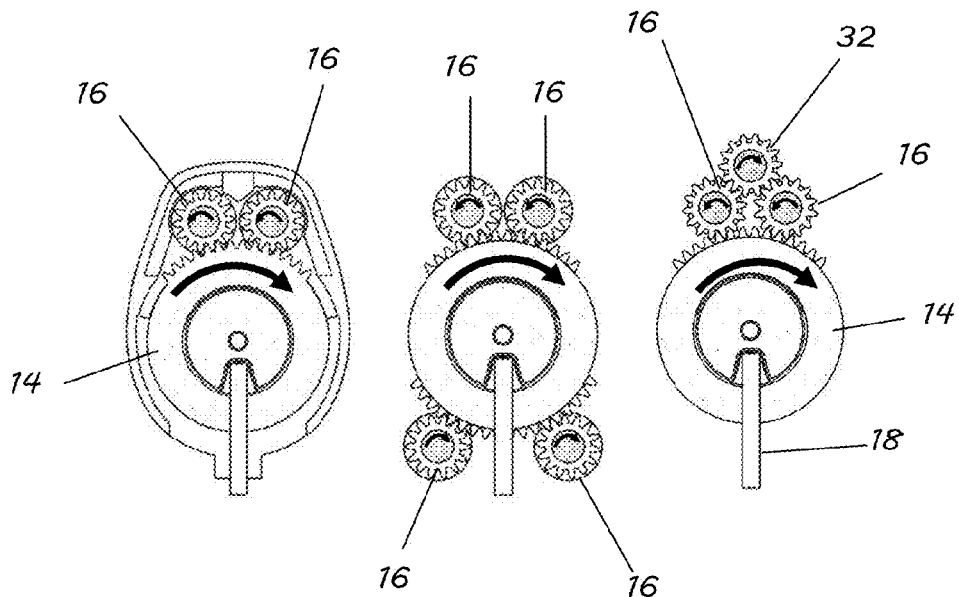
FIG. 4 is a partial view of the brush head of FIG. 1 showing the gear train.
FIG. 5 is a partial view of the brush head of FIG. 3 showing the gear train.
FIGS. 6 to 9 are partial views of a brush head according to further embodiments.
Figures 7, 8, 9:
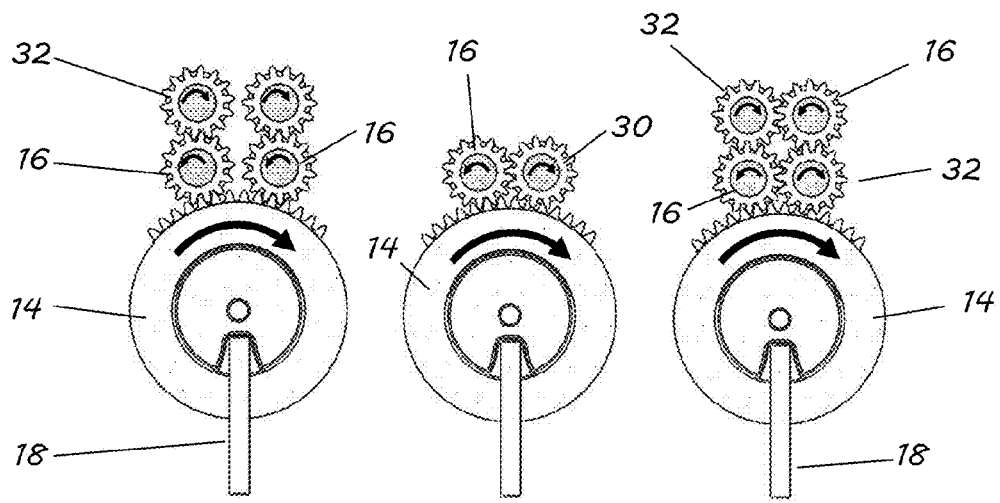
Figure 10:
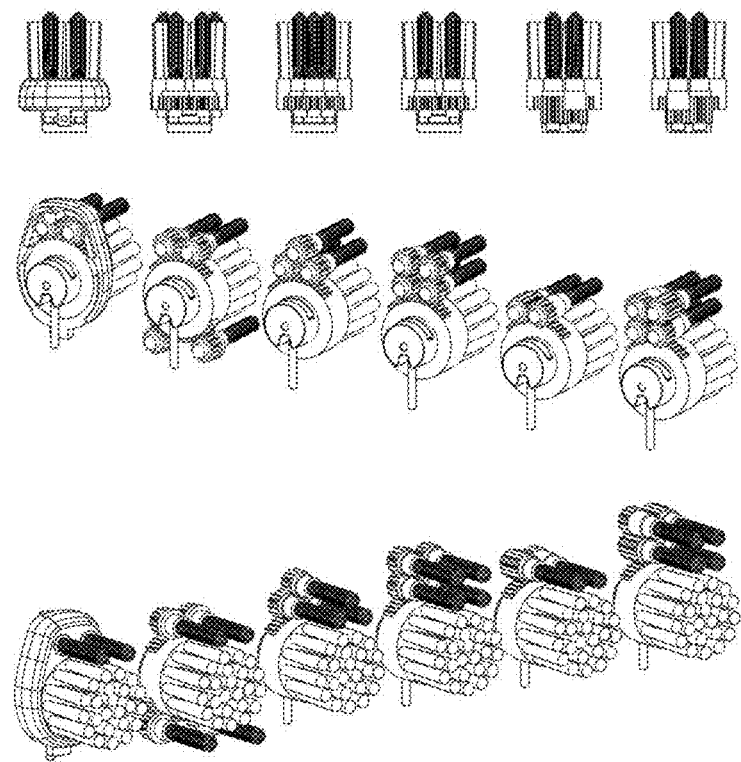
FIG. 10 shows corresponding bristle tufts to FIGS. 4 to 9 respectively.

Referring to FIG. 1, a brush head 10 for an electric toothbrush (not shown) is shown. It will be understood that the brush head may be removably connectable to a body or handle of the electric toothbrush wherein the body or handle includes a motor and means to power the motor. The brush head 10 includes a housing 11 enclosing a gear train 12. The housing 11 may be made from suitable water impermeable material, such as polypropylene, acrylonitrile butadiene styrene (ABS) or other suitable thermoplastic. The gear train 12 includes a drive gear 14 and a plurality of primary driven gears 16. The present embodiment shows two primary driven gears 16; however, it will be appreciated that more primary driven gears may also be suitable. For example, FIGS. 3 and 5 illustrate a drive gear 14 and four primary driven gears 16. Each primary driven gear 16 is configured to mesh directly with the drive gear 14. A drive shaft 18 imparts motion from the motor to the drive gear 14. The drive shaft 18 includes a first end (not shown) connectable to the motor and a second end 22 connectable to the gear train 12 and configured to provide oscillatory motion to the gear train 12. As will be understood, when the drive gear 14 moves in a clockwise direction, the primary driven gears 16 move in a counter clockwise direction. Similarly when the drive gear 14 moves in a counter clockwise direction the primary driven gears 16 move in a clockwise direction.

Figure 1A:
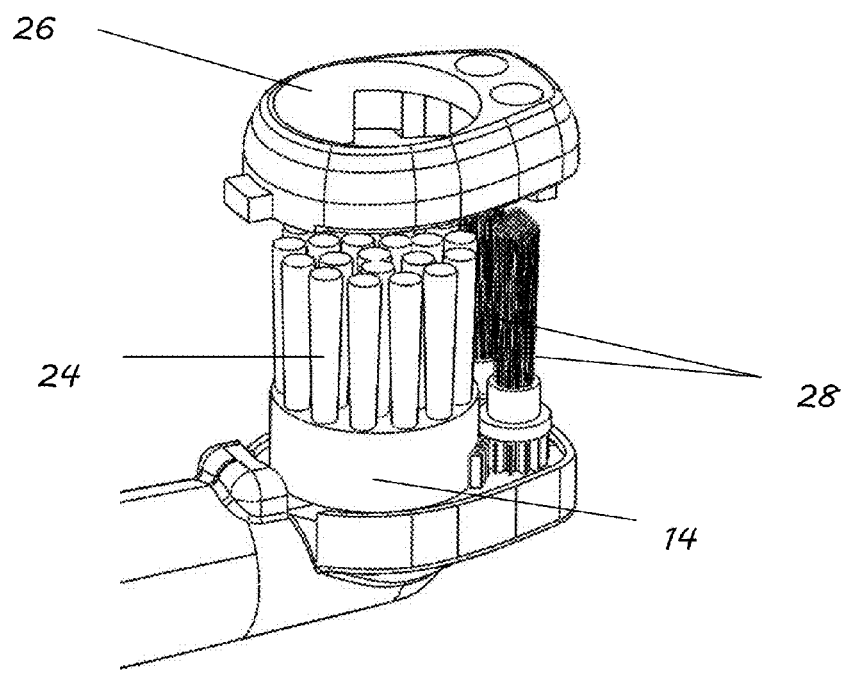
FIG. 1A is a partial perspective view of the brush head of FIG. 1.
Figure 2:
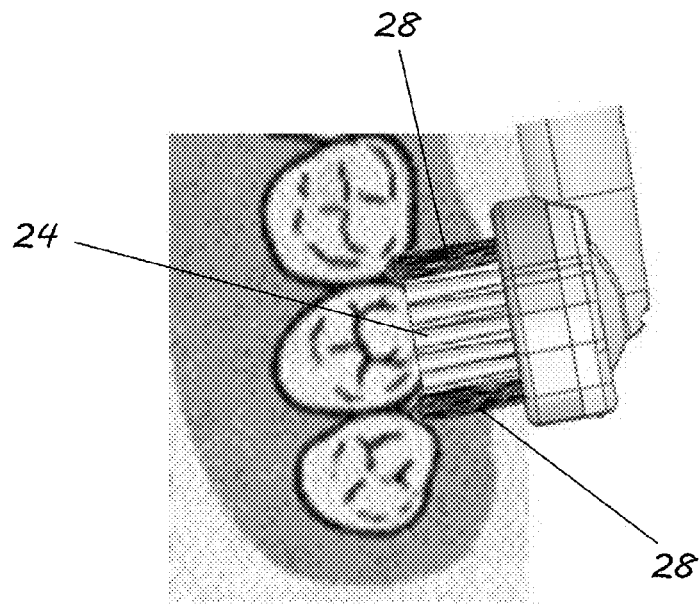
FIG. 2 is a partial view of the brush head of FIG. 1 in use.

As best shown in FIG. 1A the drive gear 14 includes a plurality of first bristle tufts 24 attached to the drive gear 14 and extending upwardly through apertures 26 in the housing. A plurality of second bristle tufts 28 is attached to each respective primary driven gear 16. In the present embodiment the first bristle tufts 24 are shorter than the second bristle tufts 28. Each first bristle tuft 24 includes a flat surface 20 suitable for cleaning the surface of a tooth. The longer, second bristle tufts 28 include a tapered tip 30 which is suitable for cleaning between teeth and along the gum line. As best shown in FIG. 2, the configuration of the bristle tufts 24, 28 allows the shorter, first bristle tufts 24 to engage the surface of a tooth while the longer, second bristle tufts 28 reach between adjacent teeth. The simultaneous oscillation and counter oscillation of the bristle tufts 24, 28 act to thoroughly clean the tooth.

The preferred gear ratio between the drive gear 14 and the driven gears 16 is 4. However, other gear ratios ranging from 1 to 6 may be suitable.

In other embodiments the gear train 12 may include one or more secondary driven gears 32. Each secondary driven gear 32 meshes directly with one or more primary driven gears 16. FIGS. 4-10 illustrate possible gear configurations. It will be understood that increasing the number of primary driven gears 16 and secondary driven gears 32 results in increased oscillation and counter oscillation thus providing more effective cleaning.

Figure 11:
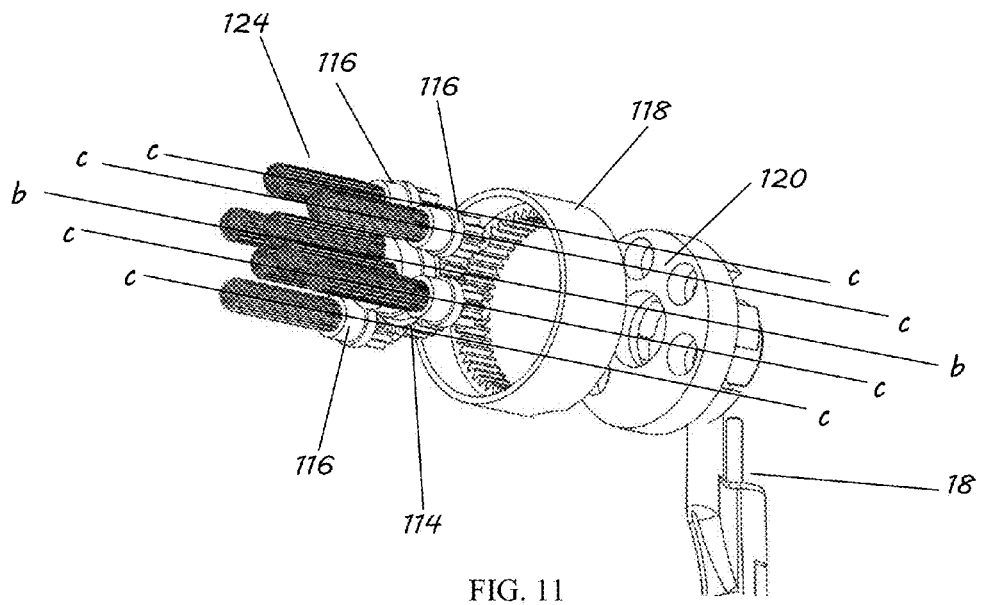
FIG. 11 is a partial exploded perspective view of a brush head according to another embodiment of the present invention.
Figure 12:
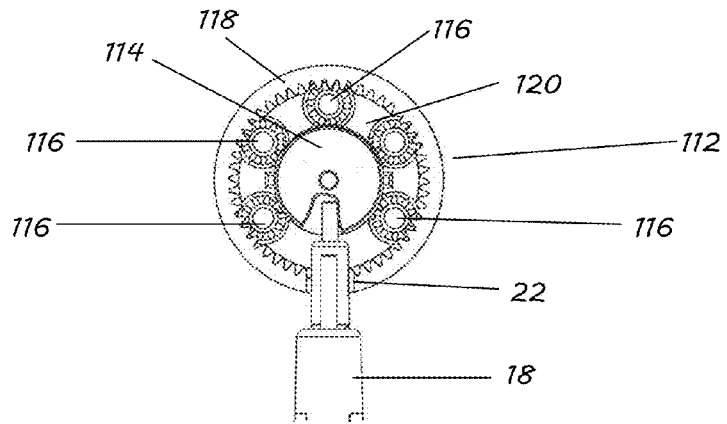
FIG. 12 is a partial view of the brush head of FIG. 11 showing the gear arrangement.
Figure 13:
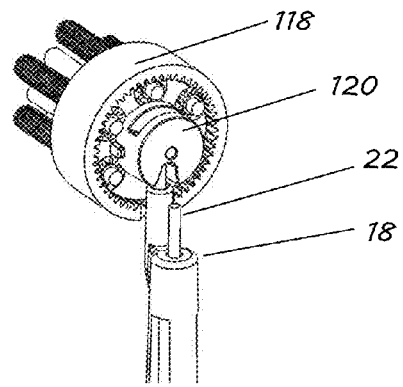
FIG. 13 is a partial view of the brush head of FIG. 11.

FIGS. 11-13 illustrate another embodiment of a brush head according to the present invention. As explained above, the brush head 10 may be removably connectable to a body or handle of an electric toothbrush. In this embodiment the brush head 10 includes a gear train 112 in the form of an epicyclic gear set. The epicyclic gear set 112 includes a sun gear 114, a plurality of planet gears 116 and a fixed ring gear 118. In the present embodiment there are five planet gears 116. Preferably, the gear ratio between the ring gear 118 and the planetary gears 116 is 5, and the gear ratio between the sun gear 114 and the planetary gears is 3. It will be appreciated that the number of planet gears 116 and the gear ratios may be varied to accommodate the size of the brush head 10. The planet gears 16 are supported by a planet carrier 120. A drive shaft 18 which is driven by a motor (not shown) includes an eccentric end 22 to provide oscillatory motion to the carrier 120. The fixed ring gear 118 is configured to mesh with the planet gears 116 so that when the planet carrier 118 oscillates, the planet gears 116 orbit around the planet carrier axis b-b and oscillate around their respective axes c-c in a direction counter to the direction of the planet carrier 120. The sun gear 114 is driven by the planet gears 116 and oscillates around its respective axis b-b in a direction counter to the direction of the planet gears 116.

As best shown in FIG. 11 the sun gear and each planet gear 116 include a bristle tuft 124. It will be understood that the bristle tufts of the planet gears may be the same as, softer or harder than the bristle tufts on the sun gear. The oscillation and counter oscillation of the bristle tufts 124 provide more effective cleaning.

Figure 14:
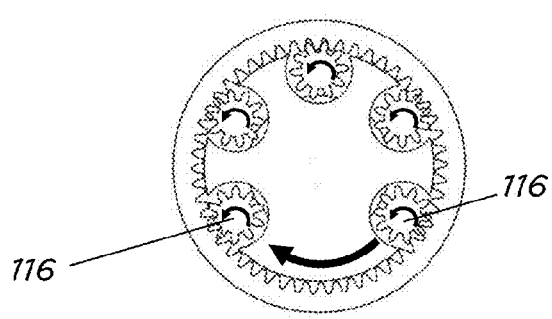
FIG. 14 is a partial view of the brush head according to another embodiment of the present invention.
Figure 15:
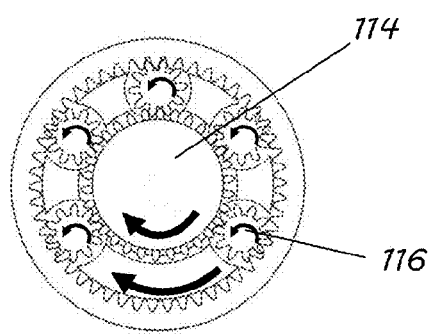
FIG. 15 is a partial view of the brush head of FIG. 11 showing the gear arrangement.

Alternatively, as shown in FIG. 14, the planet carrier 120 may be directly driven by the drive shaft 18. Bristle tufts 124 are attached to the planet carrier 120 and to each planet gear 116. This configuration provides a first drive output including the planet carrier oscillating a first axis, and a second drive output including each planet gear orbiting about the first axis and oscillating about its respective axis.

Although the invention has been described with references to specific examples, persons skilled in the art will appreciate that the invention can be embodied in other forms.

The invention claimed is:

1. A brush head for an electric toothbrush, the brush head including:
   a housing;
   a plurality of bristle tufts extending through an aperture in the housing;
   a gear train within the housing, the gear train including a drive gear configured to oscillate about an axis, and a plurality of first driven gears, each first driven gear meshed directly with the drive gear, each first driven gear being smaller than the drive gear;
   drive means configured to provide motion to the gear train;
   the drive gear providing a first drive output including a first oscillating motion in a first direction; and
   the driven gears each providing a second drive output including a second oscillating motion in a second direction which is opposite to the first direction;
   wherein the plurality of bristle tufts includes a first set of bristle tufts attached to the drive gear and a second set of bristle tufts attached to the plurality of first driven gears, each second set of bristle tufts having a tapered tip and extending axially from the plurality of first driven gears.

2. The brush head according to claim 1, wherein the plurality of first driven gears includes two first driven gears disposed around a first quadrant of the drive gear.

3. The brush head according to claim 2, wherein the plurality of first driven gears further includes two first driven gears disposed around a second quadrant opposite the first quadrant of the drive gear.

4. The brush head according to claim 1, wherein a gear ratio between the drive gear and each first driven gear is four.

5. The brush head according to claim 1, wherein the gear train includes a plurality of secondary driven gears meshed with one or more of the plurality of first driven gears.

6. The brush head according to claim 1, wherein the first set of bristle tufts are shorter than the second set of bristle tufts and wherein the first set of bristle tufts includes bristle tufts having a flat tip.

7. A brush head for an electric toothbrush, the brush head including:
   a housing;
   a plurality of bristle tufts extending through apertures in the housing;

an epicyclic gear set within the housing, the gear set including a ring gear, and plurality of planet gears supported on a planet carrier, each planet gear meshed with the ring gear;
drive means configured to provide motion to the epicyclic gear set;
a first drive output including a first oscillating motion about a first axis; and
a second drive output including an orbiting motion about the first axis and a second oscillating motion;
wherein the drive means includes a drive shaft having a first end connected to a motor and a second end connected to the planet carrier so that in use the planet carrier is driven by the drive shaft.

8. The brush head according to claim 7, wherein the plurality of bristle tufts includes a first set of bristle tufts attached to the planet carrier and a second set of bristle tufts attached to each planet gear.

9. The brush head according to claim 7, further comprising a sun gear, and wherein each planet gear is meshed between the sun gear and the ring gear.

10. The brush head according to claim 9, wherein the ring gear is fixed and the sun gear and the planet carrier oscillate about the first axis causing the plurality of planet gears to orbit about the first axis and oscillate about their own respective axes.

11. The brush head according to claim 9, wherein a gear ratio between the ring gear and the planet gear is 5, and a gear ratio between the sun gear and the planet gears is 3.

12. The brush head according to claim 9, wherein the plurality of bristle tufts includes a first set of bristle tufts attached to the sun gear and a second set of bristle tufts attached to each planet gear.

\* \* \* \* \*